(12) United States Patent
Holland

(10) Patent No.: US 10,939,813 B2
(45) Date of Patent: Mar. 9, 2021

(54) OTOSCOPE

(71) Applicant: Throat Scope Pty Ltd, Brisbane (AU)

(72) Inventor: Jennifer Louise Holland, Brisbane (AU)

(73) Assignee: Throat Scope Pty Ltd, Brisbane (AU)

( * ) Notice: Subject to any disclaimer, the term of this patent is extended or adjusted under 35 U.S.C. 154(b) by 0 days.

(21) Appl. No.: 16/333,915

(22) PCT Filed: Sep. 15, 2017

(86) PCT No.: PCT/AU2017/051007
§ 371 (c)(1),
(2) Date: Mar. 15, 2019

(87) PCT Pub. No.: WO2018/049480
PCT Pub. Date: Mar. 22, 2018

(65) Prior Publication Data
US 2019/0200850 A1    Jul. 4, 2019

(30) Foreign Application Priority Data

Sep. 16, 2016  (AU) ................................ 2016903740

(51) Int. Cl.
| | |
|---|---|
| *A61B 1/227* | (2006.01) |
| *A61B 1/00* | (2006.01) |
| *A61B 1/06* | (2006.01) |

(52) U.S. Cl.
CPC .......... *A61B 1/227* (2013.01); *A61B 1/00096* (2013.01); *A61B 1/00165* (2013.01); *A61B 1/00188* (2013.01); *A61B 1/0669* (2013.01); *A61B 1/00029* (2013.01); *A61B 1/00034* (2013.01); *A61B 1/00105* (2013.01)

(58) Field of Classification Search
CPC . A61B 1/227; A61B 1/00096; A61B 1/00165; A61B 1/00188; A61B 1/0669; A61B 1/00029; A61B 1/00034; A61B 1/00105
USPC ........................................................ 600/200
See application file for complete search history.

(56) References Cited

U.S. PATENT DOCUMENTS

| | | | |
|---|---|---|---|
| 2,240,402 A | | 4/1941 | Joroslow |
| 3,848,587 A | | 11/1974 | Mcdonald |
| 4,643,171 A | * | 2/1987 | Riester ..................... A61B 1/07 |
| | | | 600/200 |
| 5,318,009 A | | 6/1994 | Robinson |
| 2001/0037050 A1 | * | 11/2001 | Lemperle ........... A61B 1/00105 |
| | | | 600/135 |

(Continued)

FOREIGN PATENT DOCUMENTS

| | | |
|---|---|---|
| CN | 202218867 U | 5/2012 |
| FR | 2843871 B1 | 11/2004 |
| WO | 2012021937 A1 | 2/2012 |

*Primary Examiner* — Eduardo C Robert
*Assistant Examiner* — David C Comstock
(74) *Attorney, Agent, or Firm* — Oppenhuizen Law PLC; David L. Oppenhuizen

(57) ABSTRACT

The present invention relates to an otoscope for illuminating the outer ear and to methods of using the otoscope. In one embodiment, the otoscope includes a handle including a light source; and a speculum extending relative to the handle for directing light from the light source to illuminate the outer ear; wherein the speculum includes a lens for magnifying the outer ear, or a lens engager for releaseably engaging a lens.

20 Claims, 14 Drawing Sheets

(56) References Cited

U.S. PATENT DOCUMENTS

| | | |
|---|---|---|
| 2003/0195391 A1 | 10/2003 | Shin |
| 2004/0186352 A1* | 9/2004 | Roberts .................. A61B 1/227 |
| | | 600/200 |
| 2011/0015489 A1* | 1/2011 | Raghuprasad ......... A61B 1/227 |
| | | 600/187 |
| 2011/0295073 A1 | 12/2011 | Truong et al. |
| 2012/0059224 A1 | 3/2012 | Wellen et al. |
| 2013/0023914 A1 | 1/2013 | Truong et al. |
| 2015/0201869 A1* | 7/2015 | Nikzad ................... A61B 5/00 |
| | | 600/559 |
| 2015/0351607 A1* | 12/2015 | Ruppersberg ...... A61B 1/00009 |
| | | 600/473 |

\* cited by examiner

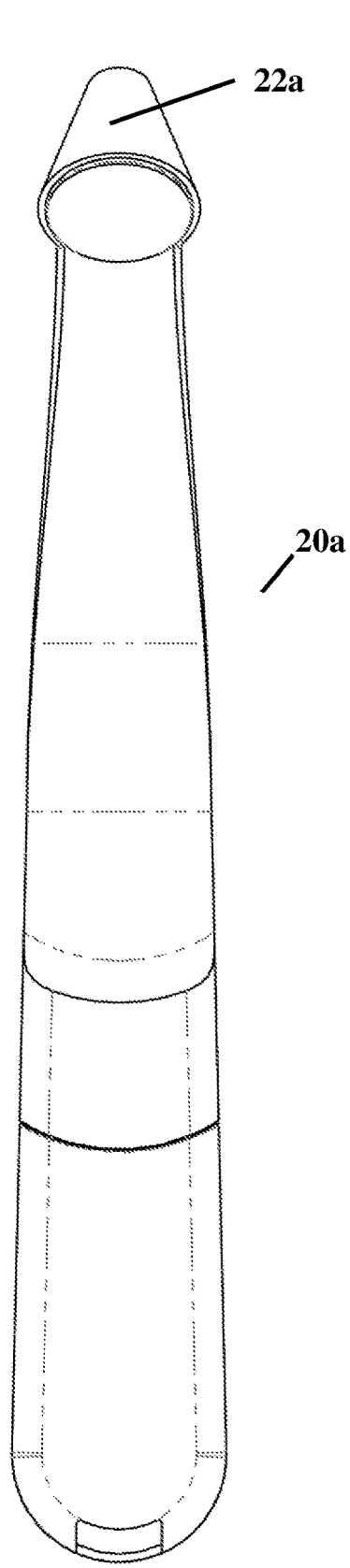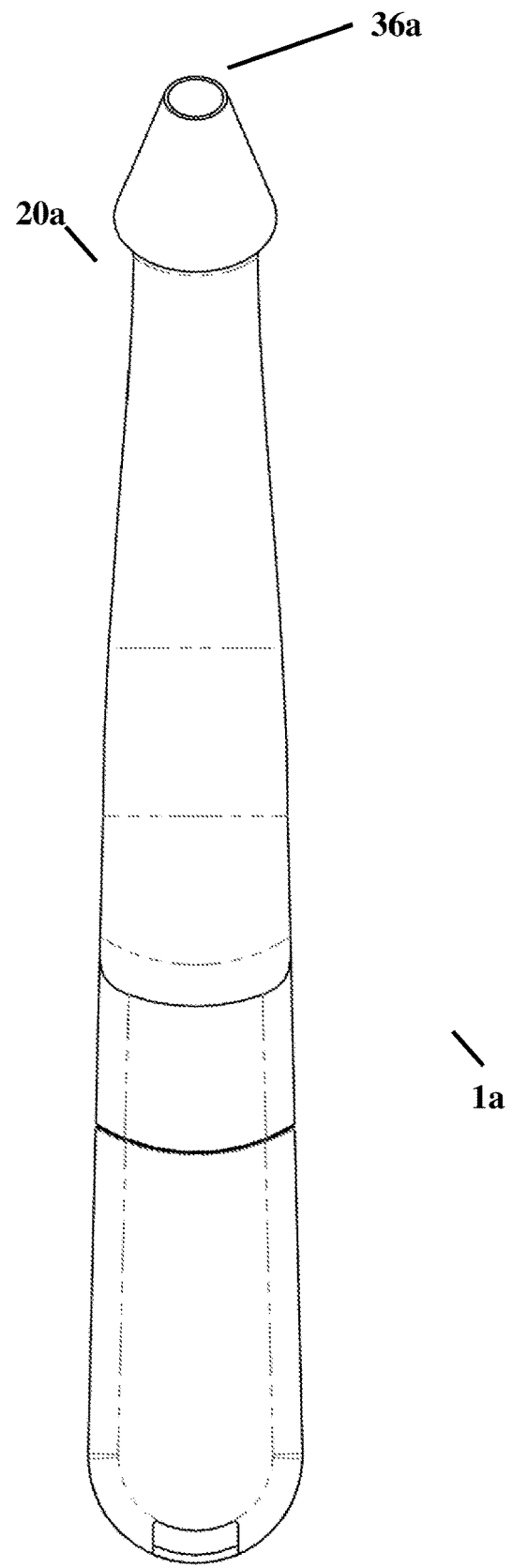
Figure 8                              Figure 9

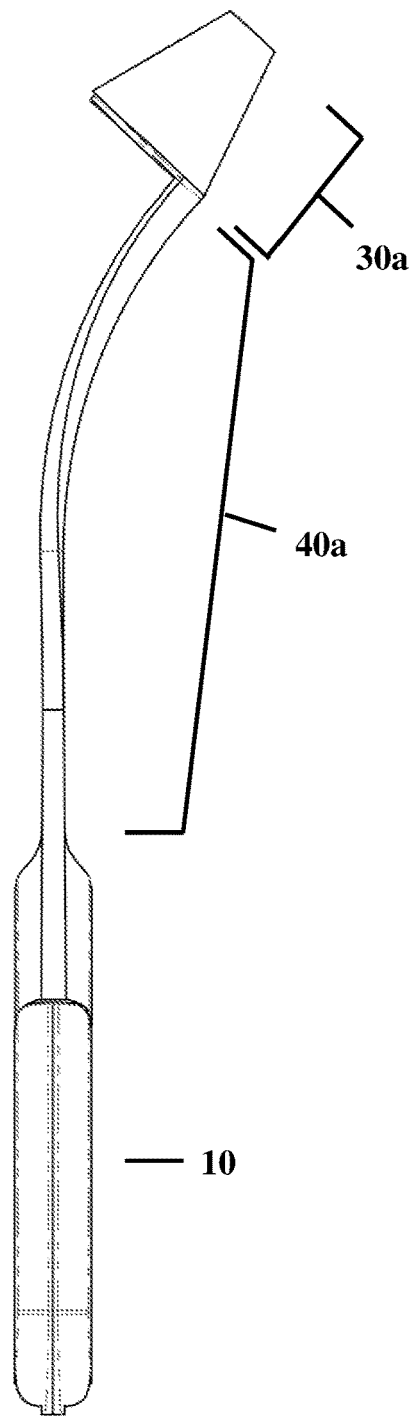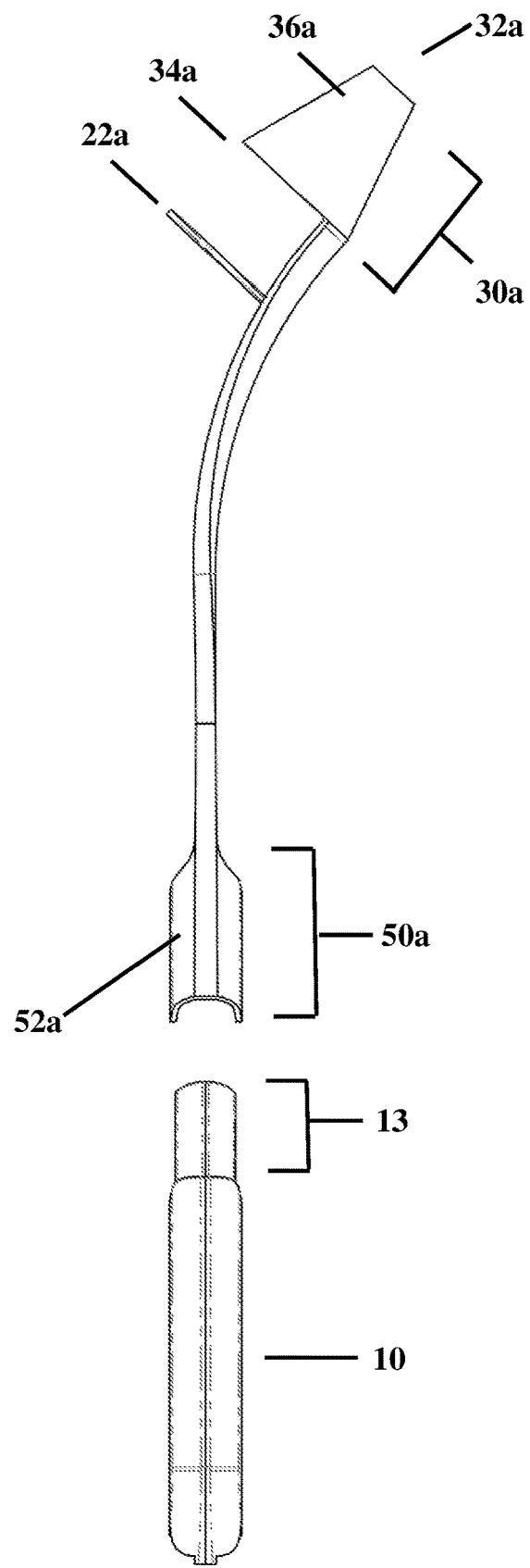
Figure 10
Figure 11

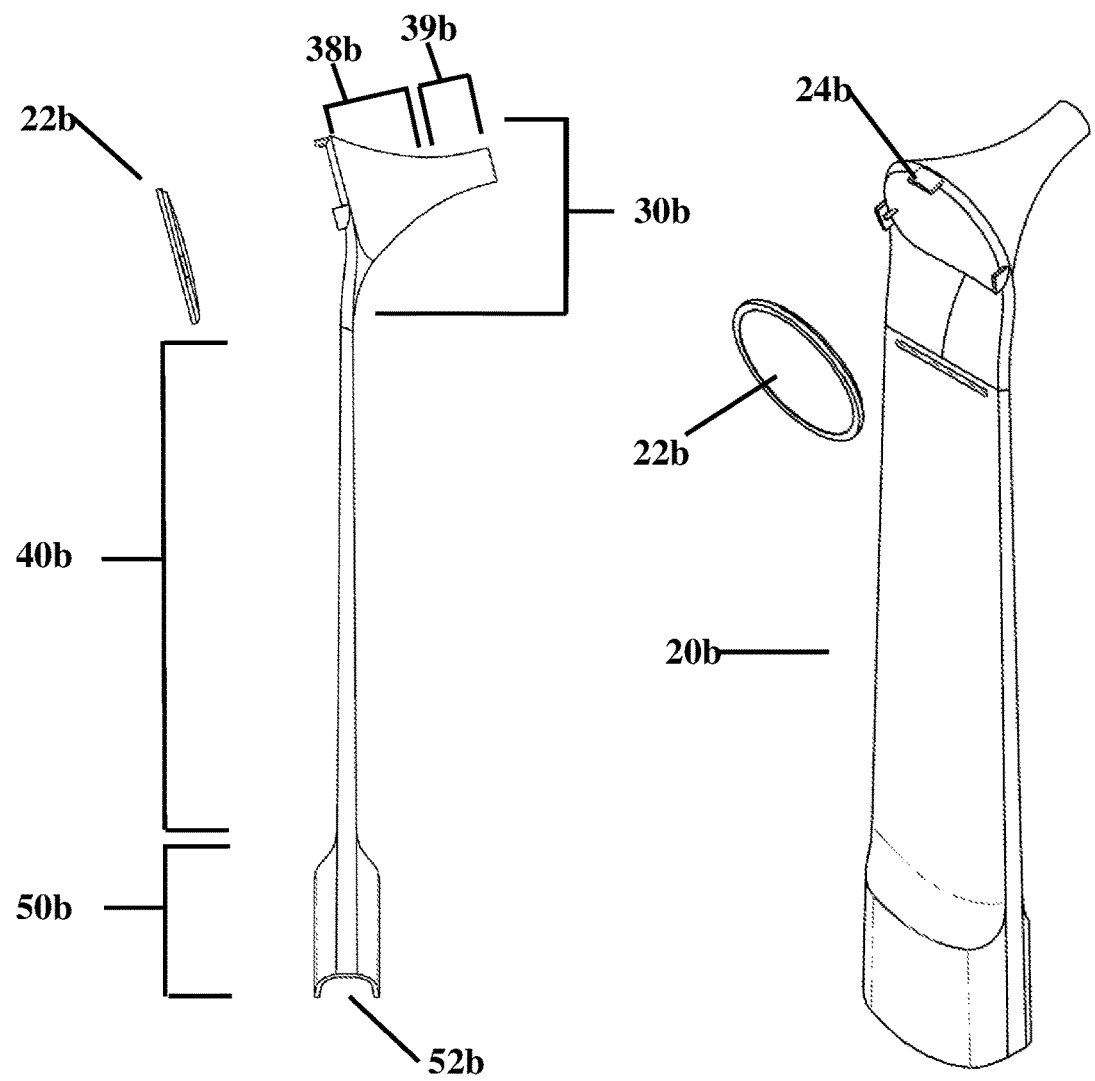
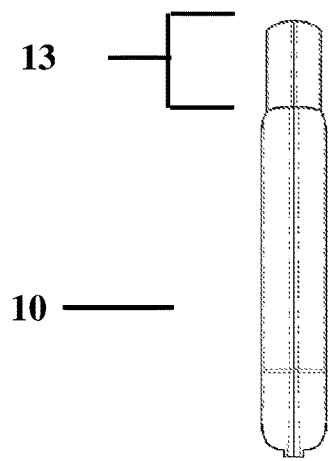
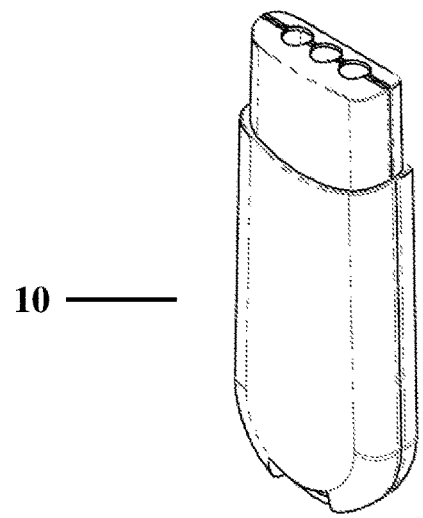
Figure 16　　　　　Figure 17

OTOSCOPE

CROSS REFERENCE TO RELATED APPLICATIONS

This is a National Stage of International Application No. PCT/AU2017/051007, filed Sep. 15, 2017, which claims the priority of Australian Application No. 2016903740, filed Sep. 16, 2016, the entire disclosures of which are hereby incorporated by reference in their entirety.

TECHNICAL FIELD

The present invention relates to a device for illuminating the outer ear, especially an otoscope, and to parts of the device and to methods of using the device.

BACKGROUND ART

The reference to any prior art in this specification is not, and should not be taken as an acknowledgement or any form of suggestion that the prior art forms part of the common general knowledge.

Otoscopes are used to visually examine the eardrum (the tympanic membrane) and parts of the outer ear canal (the external acoustic meatus). Otoscopes typically include a handle, a source of illumination, and a head having a lens and to which a speculum may be attached. When a user uses an otoscope to view a patient's outer ear, the user typically turns on the light, and looks into the lens at one end of the head and thereby through the speculum at the other end of the head. However, this arrangement typically narrows the user's field of view to the small opening at the end of the speculum. This allows a user to only inspect a relatively small portion of the outer ear canal and eardrum at any one time. Otoscopes are also typically relatively complex devices, and can be relatively expensive.

SUMMARY OF INVENTION

In one aspect, the present invention is directed to an otoscope that is easy to use, relatively simple to manufacture and/or which in use allows for visualisation of a greater portion of the outer ear canal than a traditional otoscope. In another aspect, the present invention is directed to an otoscope which may at least partially overcome at least one of the abovementioned disadvantages or provide the consumer with a useful or commercial choice.

In a first aspect, the present invention relates to an otoscope for illuminating the outer ear, the otoscope including:
 a. A handle including a light source; and
 b. A speculum extending relative to the handle for directing light from the light source to illuminate the outer ear; wherein the speculum includes a lens for magnifying the outer ear, or a lens engager for releaseably engaging a lens.

Advantageously, in a typical otoscope the lens and the speculum are positioned at opposite ends of the otoscope head. If the speculum includes the lens in use, then the lens may be positionable closer to the outer ear, avoiding visual obstruction due to the otoscope head. This also may permit a user to view a greater proportion of the outer ear than would be possible with a traditional otoscope.

Furthermore, in some embodiments having a speculum which includes a lens or a lens engager for releasably engaging a lens may allow the otoscope to not include a head. This may permit the otoscope to include fewer parts which may reduce manufacturing costs.

As used herein, the term "outer ear" may include one or more of the tragus, the anti tragus, the intertragic notch, the concha cavum, the eardrum (the tympanic membrane) and the outer ear canal (the external acoustic meatus). The "outer ear" may especially include the eardrum and/or the outer ear canal (which may be all of the outer ear canal or at least a portion of the outer ear canal, as inspected without moving the otoscope in the ear).

As used herein, the term "speculum" refers to a portion of the otoscope that is intended to contact a patient's ear. At least part of the speculum is intended to contact the outer ear of the patient when the otoscope is in use. At least part of the speculum may be insertable into a patient's outer ear canal (the external acoustic meatus). When the speculum is removable from the remainder of the otoscope, the term "speculum" refers to the entire removable portion, and not just to the portion of the otoscope that is intended to contact the patient's ear.

The speculum may be of any suitable shape. The speculum may include a distal end portion (the portion at the end furthest from the handle). The distal end portion may include a terminal end (the end furthest from the handle). The distal end portion may include a non-terminal end (the end of the distal end portion opposite to the terminal end). The distal end portion may include at least one side wall. The at least one sidewall may extend from the terminal end to the non-terminal end. The at least one side wall may be substantially circular, especially circular, more especially substantially conical. The at least one side wall may include a substantially conical portion and a substantially cylindrical portion. The substantially cylindrical portion may be located at the distal end portion terminal end. The substantially conical portion may be located at the distal end portion non-terminal end. The at least one side wall may define a visualisation passageway through the distal end portion or between the terminal end and the non-terminal end. The terminal end and the non-terminal end may each define an aperture. The aperture at the terminal end may be of smaller diameter than the aperture at the non-terminal end. The distal end portion may define an aperture at the terminal end, and include a lens or a lens engager at the non-terminal end. The diameter of the aperture at the terminal end may be smaller than the diameter of the lens (or the lens to be engaged) at the non-terminal end. The speculum, or the distal end portion, may be sized depending on the size of the ear to be inspected. For example, a neonatal ear may require a significantly smaller distal end portion than an adult ear.

The distal end portion may include the lens or the lens engager. The lens may be located or locatable at one end of the visualisation passageway, especially at the non-terminal end of the distal end portion. The lens may or may be positioned to abut or adjoin the at least one sidewall. The lens or lens engager may be integral with the speculum. The lens or lens engager may be integral with the distal end portion. If the speculum includes a lens engager, the speculum may also include a lens. The lens or lens engager may be positioned to provide a gap between the distal end portion of the speculum and the lens. Advantageously, a gap may decrease or prevent light from passing up the medial portion of the speculum (discussed below) and directly into the lens.

The lens may be integral with the speculum, and/or may be fixed to the speculum in any suitable way. For example, the lens may be fixed to the speculum by welding (especially spin or ultrasonic welding), by mechanical fasteners (such as at least one screw), or by adhesive. The lens may be integrally formed with the speculum. For example, the lens and speculum may be moulded as a single unit.

The lens engager may be integral with the speculum. For example, the lens engager and the speculum may be moulded as a single unit. The lens engager may include a cradle for the lens. The lens engager may include a mechanical fastener (such as a clasp, clip or screw) or adhesive for fastening the lens in position. The lens engager may engage the lens by clip-fit, friction-fit, interference-fit or the like.

The lens may be convex. The lens may be less than 15, less than 12, less than 10, less than 8, less than 7, less than 6, less than 5, less than 4, less than 3 or less than 2 dioptre. The lens may be from 2 to 15 dioptre, from 3 to 12 dioptre, from 4 to 10 dioptre, or from 5 to 9 dioptre. The lens may be about 6 to 10 dioptre, especially about 8 dioptre.

The speculum may include a proximate end portion (closest to the handle) and/or a medial portion (between the distal and proximate end portions). The medial portion (and/or the proximate end portion) may be straight or curved. The medial portion (and/or the proximate end portion) may be relatively thin. The medial portion (and/or the proximate end portion) may be curved or substantially straight or substantially flat in a lateral direction. The medial portion (and/or the proximate end portion) may transition from flat or straight to increasingly curved in a lateral direction as the medial portion extends from the proximate end portion to the distal end portion. The medial portion (and/or the proximate end portion) may be substantially flat or curved in a longitudinal direction. The medial portion may be inclined relative to the proximate end portion in a longitudinal direction. The longitudinal axis of the distal end portion may be substantially parallel with the longitudinal axis of the handle, or the longitudinal axis of the proximate end portion. The medial portion (and/or the proximate end portion) may be curved to position the longitudinal axis of the distal end portion at more than 10° relative to the longitudinal axis of the handle, especially at more than or at about 15°, 20°, 25°, 30°, 40°, 50°, 60°, 70°, 80° or 90° relative to the longitudinal axis of the handle. The medial portion may be curved to position the longitudinal axis of the distal end portion at from 15° to 35°, especially from 20° to 30°, especially about 25°, relative to the longitudinal axis of the handle. The medial portion may be curved to position the longitudinal axis of the distal end portion at from 45° to 120°, especially from 55° to 100° or from 65° to 85°, more especially about 75° or about 90°, relative to the longitudinal axis of the handle.

In another embodiment, the longitudinal axis of the distal end portion is at more than 10° relative to the longitudinal axis of the handle or the longitudinal axis of the proximate end portion, especially at more than or at about 15°, 20°, 25°, 30°, 40°, 50°, 60°, 70°, 80° or 90° relative to the longitudinal axis of the handle or the longitudinal axis of the proximate end portion. The longitudinal axis of the distal end portion may be at from 15° to 35°, especially from 20° to 30°, especially about 25°, relative to the longitudinal axis of the handle or the longitudinal axis of the proximate end portion. The longitudinal axis of the distal end portion may be at from 45° to 120°, especially from 55° to 100° or from 65° to 85°, more especially about 75° or about 90°, relative to the longitudinal axis of the handle or the longitudinal axis of the proximate end portion.

In one embodiment, the speculum is adapted to direct light from the light source to illuminate the outer ear. In a further embodiment, the speculum is for (or is adapted to) focussing light from the light source to illuminate the outer ear. In another embodiment, light from the light source may pass through the speculum to illuminate the outer ear.

The speculum may direct light from the light source to illuminate the outer ear in any suitable way. The speculum may be configured (or adapted) to emit light from the terminal end. The speculum may be made of a light-reflective material, in which case the speculum may direct light through the visualisation passageway of the distal end portion. In one embodiment the speculum acts as an optical waveguide for light emitted from the light source. The speculum may be relatively thin, which provides a shallow angle of incidence for light impinging on an inner surface of the upper and lower faces of the speculum. This advantageously results in light travelling along the speculum to undergo a minimal number of internal reflections within the speculum so that light emitted from the light source, and especially substantially all light emitted from the light source, is emitted at the terminal end of the speculum.

In some embodiments, the surface of the speculum may be configured to control the passage of light. For example, the surface of the speculum may be smooth. This may improve internal reflection for light passing through the speculum, resulting in most, if not substantially all light passing through to the terminal end. Alternatively, the surface of the speculum may be roughened where emission of light is desired. The thickness of the speculum may also be used to control the passage of light, as the thinner the speculum the more light is expected to pass through to the terminal end.

The speculum may be configured to control where light is emitted. For example, it may be advantageous for substantially all light travelling through the speculum to pass to the terminal end. Alternatively, it may be advantageous for some light to be emitted before the terminal end so as to illuminate a greater portion of the outer ear.

The speculum may be a solid body extending from adjacent the light source to the terminal end. This may provide an optical waveguide for light emitted from the light source. The speculum distal end portion (and optionally also the medial end portion) may be a solid body providing an optical waveguide for light passing through the speculum. All or a portion of the speculum may include a reflective surface coating. Where light is to be emitted the speculum may not include the reflective surface coating. Alternatively, the speculum may include an internal cavity.

All or a portion of the speculum may be transparent or clear. A transparent speculum (especially a transparent speculum distal end portion) may be advantageous in allowing greater visibility of the outer ear. Advantageously, a transparent or clear speculum distal end portion may allow a user to view and illuminate a greater proportion of the outer ear than would be possible with a traditional otoscope. It is believed that a transparent or clear speculum distal end portion provides greater visibility to the user, as this minimises visual obstruction when illuminating an outer ear.

The speculum may be made of any suitable materials which are capable of transmitting light. For example, the speculum may be made of a plastic, especially poly(methyl methacrylate), polycarbonate or a polystyrene (especially General Purpose Polystyrene or GPPS), especially polycarbonate or a polystyrene. Advantageously, polycarbonate may be recyclable, optically transparent and is not brittle. The speculum may especially be made from an injection moulded plastic.

The speculum may be disposable. The speculum may be sterilisable. In either case, the otoscope may be handled hygienically. If the speculum is sterilisable then a sterilisation method may be selected so that, for example, the sterilisation method does not impair the function of the lens.

The otoscope, otoscope handle or speculum may include an image capture device, such as a camera. The image capture device may be for capturing an image of the patient's outer ear. The image capture device may be located, for example, in the handle, in the speculum, in the distal end portion of the speculum, or in the lens.

The speculum may extend from the otoscope handle. The speculum may be integral with the otoscope handle. The speculum may be removable from the handle. The speculum may be releasably engageable with the handle.

If the speculum is removable from the handle, the proximate end portion of the speculum may be engageable with an attachment-coupling portion of the handle. The speculum proximate end portion may be coupled to the handle using a clip-fit, friction-fit, interference-fit or the like. The attachment-coupling portion of the handle may include a cavity into which the speculum proximate end portion may be located, encapsulated or enveloped. Alternatively, the speculum proximate end portion may include a cavity into which the attachment-coupling portion of the handle may be located, encapsulated or enveloped. The speculum proximate end portion may include one or more projections or depressions which cooperate with corresponding depressions or projections on the handle attachment-coupling portion. In one embodiment, the speculum includes a proximate end portion including a cavity, and a portion of the handle is insertable into the cavity.

In another embodiment, the speculum may extend from an intermediate waveguide. The intermediate waveguide may act as a waveguide for light emitted from the light source. The speculum may be releasably engageable with the intermediate waveguide. The intermediate waveguide may be releaseably engageable with the handle. The intermediate waveguide may be integral with the handle. The intermediate waveguide may be a solid body extending from adjacent the light source to a distal portion of the intermediate waveguide (a portion furthest away from the handle), or to a portion of the intermediate waveguide at which the speculum may be releaseably engaged. All or a portion of the intermediate waveguide may include a reflective surface coating. Alternatively, the intermediate waveguide may include an internal cavity.

The intermediate waveguide may include one or more of a proximate end portion (a portion closest to the handle), a distal end portion (a portion furthest from the handle) and a medial portion (a portion between the proximate and distal end portions). The intermediate waveguide may be a blade. The distal end portion and/or the medial portion of the intermediate waveguide may be substantially flat. The distal end portion and/or the medial portion of the intermediate waveguide may be substantially planar. The intermediate waveguide may be suitable for use as the blade of a tongue depressor.

The speculum may be releaseably engageable with the distal end portion of the intermediate waveguide. For example, the speculum proximate end portion may encapsulate or envelop at least a portion of the intermediate waveguide, especially at least a portion of the distal end portion of the intermediate waveguide. The speculum proximate end portion may be a sleeve into which a portion of the intermediate waveguide may be inserted. The speculum proximate end portion may be releaseably engageable with the intermediate waveguide in any suitable way, including by clip-fit, friction-fit, interference-fit or the like.

The proximate end portion of the intermediate waveguide may be releaseably engageable with an attachment-coupling portion of the handle. The proximate end portion of the intermediate waveguide may be coupled to the handle using a clip-fit, friction-fit, interference-fit or the like. The attachment-coupling portion of the handle may include a cavity into which the proximate end portion of the intermediate waveguide may be located, encapsulated or enveloped. Alternatively, the proximate end portion of the intermediate waveguide may include a cavity into which the attachment-coupling portion of the handle may be located, encapsulated or enveloped. The proximate end portion of the intermediate waveguide may include one or more projections or depressions which cooperate with corresponding depressions or projections on the handle attachment-coupling portion.

All or a portion of the intermediate waveguide may be transparent or clear. The intermediate waveguide may be made of any suitable materials which are capable of transmitting light. For example, the intermediate waveguide may be made of a plastic, especially poly(methyl methacrylate), polycarbonate or a polystyrene (especially General Purpose Polystyrene or GPPS); especially polycarbonate or a polystyrene. Advantageously, polycarbonate or a polystyrene may be recyclable, optically transparent and is not brittle. The intermediate waveguide may especially be made from an injection moulded plastic. The intermediate waveguide may be disposable. The intermediate waveguide may be sterilisable.

The handle may include a switch to connect a power supply to the light source. The switch may be multi-positionable, and may especially allow variable intensities of light to be emitted from the light source.

Coupling the speculum to the handle may actuate the switch so that light emitted from the light source is transmitted by the speculum to the outer ear when the handle and speculum are coupled together. Advantageously, this arrangement permits simple operation by a user, such as medical personnel or a member of the general public, by allowing the user to activate the light source by simply coupling the handle and speculum together, thereby avoiding the need to actuate a separate switch and making the otoscope easier to use. Alternatively, coupling the intermediate waveguide to the handle may actuate the switch so that light emitted from the light source is transmitted to the distal end portion of the intermediate waveguide when the handle and intermediate waveguide are coupled together. Coupling the speculum to the intermediate waveguide may then result in the light emitted from the intermediate waveguide to be transmitted to the distal end portion of the speculum to thereby illuminate an outer ear. In one embodiment, the speculum is releaseably engageable with the handle, and coupling the speculum to the handle activates the light source to transmit light to a terminal end of the speculum.

In one embodiment, the speculum proximate end portion (or the intermediate waveguide proximate end portion) includes a cavity and includes a projection within the cavity for actuating the switch when the handle and speculum (or intermediate waveguide) are coupled together. The switch may be positioned within a recess in the attachment-coupling portion of the handle, so that the projection enters the recess and engages the switch when the handle and speculum (or intermediate waveguide) are coupled together. In this way the light source may be activated.

In another embodiment, the attachment-coupling portion of the handle includes a switch. The proximate end portion of the speculum (or proximate end portion of the intermediate waveguide) may include a cavity, and the attachment-coupling portion may be slideable inside the cavity. Sliding the attachment-coupling portion inside the cavity may actuate the switch. In this way the light source may be activated. The attachment-coupling portion may include an outer wall having a flap, and the flap may be positioned over the switch, so that depression of the flap (by coupling the attachment-coupling portion and the cavity) actuates the switch.

In a further embodiment, the handle attachment-coupling portion may include a cavity, and the proximate end portion of the speculum (or intermediate waveguide) may be slideable inside the cavity. Sliding the proximate end portion inside the cavity may actuate the switch. In this way the light source may be activated. The switch may be inside the cavity.

Alternatively, the switch may be located on the exterior of the handle, so that the switch may be actuated by the user after the handle and speculum (or handle and intermediate waveguide) are coupled together.

One or more of the speculum, intermediate waveguide and handle (especially the speculum and/or handle) may include at least one depression or projection to assist a user in handling the otoscope, and in particular in decoupling the speculum, intermediate waveguide and/or handle from each other. For example, the speculum, intermediate waveguide and/or handle may include a plurality of projections or depressions, most especially a plurality of ridges. In one embodiment, the proximate end portion of the speculum includes a plurality of ridges on at least one side wall opposite to the inner side wall of the cavity. In another embodiment, the proximate end portion of the intermediate waveguide includes a plurality of ridges on at least one side wall opposite to the inner side wall of the cavity.

Advantageously, the presence of at least one depression or projection on the speculum may allow a user to hygienically detach the speculum from the handle without touching the portion of the speculum that has come into contact with the patient's outer ear. For example, the at least one depression or projection may be pushed or "flicked" by the user to detach the speculum. This arrangement may also be relatively simple to manufacture.

The light source may be located within, or entirely within the handle. The handle may include a handle body, and the light source may be located within, or entirely within, the handle body. The light source may be located within, or entirely within, the attachment-coupling portion of the handle. The light source may be positioned adjacent to an opening in the attachment-coupling portion of the handle, so that visible radiation from the light source passes through the opening and into the speculum (either directly or via the intermediate waveguide), thereby maximising transmission of light into the speculum.

The handle may include a plurality of light sources. In one embodiment, the handle includes 1, 2, 3, 4 or 5 light sources; especially three light sources. The light sources may be positioned so as to extend laterally across the handle. Including a plurality of spaced apart light sources may be advantageous, as this advantageously ensures that light enters the speculum or intermediate waveguide at a number of different locations, which can provide improved illumination and contrast when the otoscope is used to illuminate the outer ear of a patient.

Any suitable light source may be used in the otoscope. Exemplary light sources include an incandescent bulb (including a halogen bulb), a fluorescent lamp, a high-intensity discharge lamp, a low-pressure sodium lamp, a light-emitting diode, a gas-discharge lamp and a monatomic gas bulb such as krypton or xenon. However, typically the light source or plurality of light sources in the handle is light-emitting diodes (LEDs), such as surface mount LEDs or board mount LEDs. LEDs typically use less energy than other forms of light source, thereby maximising battery life. Additionally, LEDs typically generate less heat than other forms of light source, thereby preventing the handle from overheating. Overheating may occur, for example, if incandescent or other light sources are used, and overheating may result in distortion of the handle, intermediate waveguide and/or the speculum, or patient discomfort when the otoscope is used.

The light source may be connected to a power supply through the switch, especially on a circuit board. The circuit board may include other components, such as resistors and the like, although in one example, the circuit board consists of a light source, a switch and a connection for a power supply. The circuit may consist of, for example, three surface mounted LEDs in parallel, a switch in series and a battery.

The handle may include a power supply or power source, such as a battery. Suitable batteries for use in the otoscope may include a battery selected from: zinc-carbon, zinc-chloride, lithium, alkaline, nickel-cadmium, nickel-metal hydride, lead-acid and lithium ion, although any suitable power supply may be used. The battery may be especially a lithium-ion battery, more especially a CR2032 battery or a rechargeable lithium battery. The handle may also include a removable cover for allowing the battery to be removed and replaced as required. The handle may also include a fastener for the cover, such as a screw to secure the cover closed. The use of such a fastener may be advantageous for child safety, for example.

The power source may be rechargeable. The power source may be capable of wireless charging, such as induction charging.

In one example, the battery may be located within the portion of the handle opposite to the attachment-coupling portion of the handle, however this is not essential and any suitable position may be used. The battery may be replaceable and/or rechargeable. For example, the battery may be charged by coupling the otoscope to a power cord. In another example, the battery may be charged by inductive charging. In some examples, the battery in the otoscope is not replaceable. For example, the handle may not include a removable cover to access the battery, so that the handle is replaced when the battery is depleted. In this example, the outer shell of handle may be formed from a single piece of plastic, especially a single piece of injection moulded plastic.

In another example, the otoscope may not include a battery. For example, the light source in the otoscope may be powered by electricity from an external power supply when in use.

The handle may be made of a material such as a moulded plastic, especially a thermosetting plastic or a thermoplastic. The handle especially may be made from a material selected from: polystyrene, acrylonitrile butadiene styrene (ABS), polypropylene, polycarbonate and polymethylmethacrylate, especially acrylonitrile butadiene styrene (ABS). The handle may be especially made using an injection moulded plastic.

The handle, intermediate attachment and/or speculum may be manufactured and/or sold separately. In either case, the speculum and/or intermediate waveguide may be sold in a sterile form, for example provided sterilised in packaging, allowing the speculum or intermediate waveguide to be used as a single use disposable item. The speculum or intermediate waveguide may alternatively be sterilisable for repeated use. The handle may also be sterilisable, although in a preferred form the handle does not require sterilisation and may be repeatedly used. If the handle is sterilisable, and the handle includes a power supply and a light source, then the power supply and the light source should be selected and located so that these components will continue to function after repeated sterilisation (whether chemical or thermal sterilisation, for example). For example, it may be advantageous to employ inductive charging if the otoscope is sealed for sterilisation.

In a further example, the speculum is integrally formed with handle. In this example, the speculum is not removably coupled to the handle, and the outer shell of the speculum and handle may be formed from a single piece of plastic, especially a single piece of injection moulded plastic. In this example, the otoscope may be sterilisable for repeated use, or may be sold in a sterile form, for example provided sterilised in packaging, allowing the otoscope to be used as a single use disposable item.

In yet another example, the intermediate waveguide is integrally formed with the handle. In this example, the intermediate waveguide is not removably coupled to the handle, and the outer shell of intermediate waveguide and handle may be formed from a single piece of plastic, especially a single piece of injection moulded plastic. In this example, the handle/intermediate waveguide may be repeatedly used, may not require sterilisation, may be sterilisable for repeated use, or may be sold in a sterile form. For example, the handle/intermediate waveguide may be provided sterilised in packaging, allowing the handle/intermediate waveguide to be used as a single use disposable item.

In some examples, the handle includes a keyring attachment, allowing the handle to be easily carried by a user. The handle may then be easily attached to a speculum and/or intermediate waveguide when the otoscope is to be used.

The speculum, intermediate waveguide and handle may be of any suitable length or shape. In one embodiment, the length of handle alone may be, for example, 15 to 65 mm, especially from 20 mm to 60 mm, or from 25 to 55 mm, more especially from 30 to 50 mm, or from 35 mm to 45 mm, most especially about 40 mm. When present, the length of the attachment-coupling portion of the handle may be, for example, from 5 to 35 mm, especially from 10 to 30 mm, more especially from 15 mm to 25 mm, most especially about 20 mm.

In another example, the width of the otoscope (including the speculum, intermediate waveguide and/or the handle) is from 5 mm to 40 mm, more especially from 7 mm to 35 mm, more especially from 10 mm to 30 mm, more especially from 15 mm to 25 mm, most especially about 20 mm.

In another example, the height of the handle 4 is from 0.5 mm to 70 mm, especially from 3 mm to 35 mm, more especially from 5 mm to 20 mm, more especially from 6 mm to 12 mm, more especially about 9 mm.

The otoscope for illuminating the outer ear may be an otoscope for illuminating the outer ear of a patient. The patient may be an animal, especially a human. However, the otoscope may also be for veterinary use.

In a second aspect, the present invention relates to an otoscope for illuminating the outer ear, the otoscope including:
 a. A handle including a light source; and
 b. A speculum.

In one embodiment of the second aspect, the speculum extends the handle. In another embodiment, the speculum is for (or is adapted to) directing light from the light source to illuminate the outer ear. In a further embodiment, the speculum is for (or is adapted to) focussing light from the light source to illuminate the outer ear. In another embodiment, light from the light source may pass through the speculum to illuminate the outer ear.

In a further embodiment, the speculum includes a lens for magnifying the outer ear. In another embodiment, the speculum includes a lens engager for engaging a lens.

In one embodiment, the otoscope includes a light source, a lens or lens engager and a speculum, and the lens or lens engager is positioned intermediate the light source and the speculum.

Features of the second aspect of the present invention may be as described for the first aspect of the present invention.

In a third aspect, the present invention relates to an otoscope for illuminating the outer ear, the otoscope including:
 a. A handle which includes:
  (i). A light source; and
  (ii). A switch for connecting a power supply to the light source; and
 b. A speculum for illuminating the outer ear, the speculum being removably coupled to the handle and having a speculum cavity at one end for receiving the handle;
 wherein coupling the speculum to the handle actuates the switch so that light emitted from the light source is transmitted by the speculum to the outer ear.

Features of the third aspect of the present invention may be as described for the first and second aspects.

In a fourth aspect, the present invention relates to an otoscope for illuminating the outer ear, the otoscope including:
 a. A handle having a handle body, wherein the handle includes:
  i. A light source entirely within the handle body; and
  ii. An attachment-coupling portion including a switch for connecting a power supply to the light source; and
 b. A speculum for illuminating the outer ear, the speculum being removably coupled to the handle and including:
  i. A cavity at one end for receiving the attachment-coupling portion of the handle, and
  ii. A solid body extending from the cavity to the end distal the cavity, wherein the solid body is configured to act as an optical waveguide for light emitted from the light source;
 wherein coupling the speculum to the handle actuates the switch so that light emitted from the light source is transmitted by the speculum into the outer ear.

Features of the fourth aspect of the present invention may be as described for the first to third aspects of the present invention.

In a fifth aspect, the present invention relates to an otoscope speculum. In one embodiment, the speculum includes a lens for magnifying the outer ear. In another embodiment, the speculum includes a lens engager for engaging a lens for magnifying the outer ear.

Features of the speculum of the fifth aspect may be as described for the speculum of the first to fourth aspects.

In a sixth aspect, the present invention relates to an otoscope handle. Features of the handle of the sixth aspect may be as described for the handle of the first to fourth aspects.

In a seventh aspect, the present invention relates to a method of illuminating the outer ear of a patient, the method including the step of inserting the speculum of the otoscope of the first to fourth aspects of the present invention (or at least a portion of the distal end portion of the speculum) into the outer ear of the patient, or contacting the speculum of the otoscope of the first to fourth aspects of the present invention (or at least a portion of the distal end portion of the speculum) with the outer ear of the patient. The method may include the further step of viewing the patient's outer ear by looking through the lens.

In an eighth aspect, the present invention relates to a method of illuminating the outer ear of a patient, the method including the step of coupling the speculum to the handle to form the otoscope of the first to fourth aspects of the present invention, and to thereby actuate the switch and activate the light source. In one embodiment, the method further includes the step of inserting the speculum (or at least a portion of the distal end portion of the speculum) into the outer ear of the patient, or contacting the speculum (or at least a portion of the distal end portion of the speculum) with the outer ear of the patient. The method may include the further step of viewing the patient's outer ear by looking through the lens.

In a ninth aspect, the present invention relates to a method of illuminating the outer ear of a patient, the method including the step of coupling an intermediate waveguide of the first or second aspect of the present invention to a handle of the first or second aspect of the present invention to thereby actuate the switch and activate the light source. The method may further include the step of coupling the speculum of the first or second aspects of the present invention with the intermediate waveguide. The method may further include the step of inserting the speculum (or at least a portion of the distal end portion of the speculum) into the outer ear of the patient, or contacting the speculum (or at least a portion of the distal end portion of the speculum) with the outer ear of the patient. The method may include the further step of viewing the patient's outer ear by looking through the lens.

Any of the features described herein can be combined in any combination with any one or more of the other features described herein within the scope of the invention.

BRIEF DESCRIPTION OF DRAWINGS

Examples of the invention will now be described by way of example with reference to the accompanying Figures, in which:

FIG. 8 shows a top view of a second example otoscope;
FIG. 9 shows a bottom view of the otoscope of FIG. 8;
FIG. 10 shows a side view of the otoscope of FIG. 8;
FIG. 11 shows an exploded side view of the otoscope of FIG. 8;
FIG. 16 shows an exploded side view of the example otoscope of FIG. 13;
FIG. 17 shows an exploded perspective view of the example otoscope of FIG. 13.

Figures 1, 2:
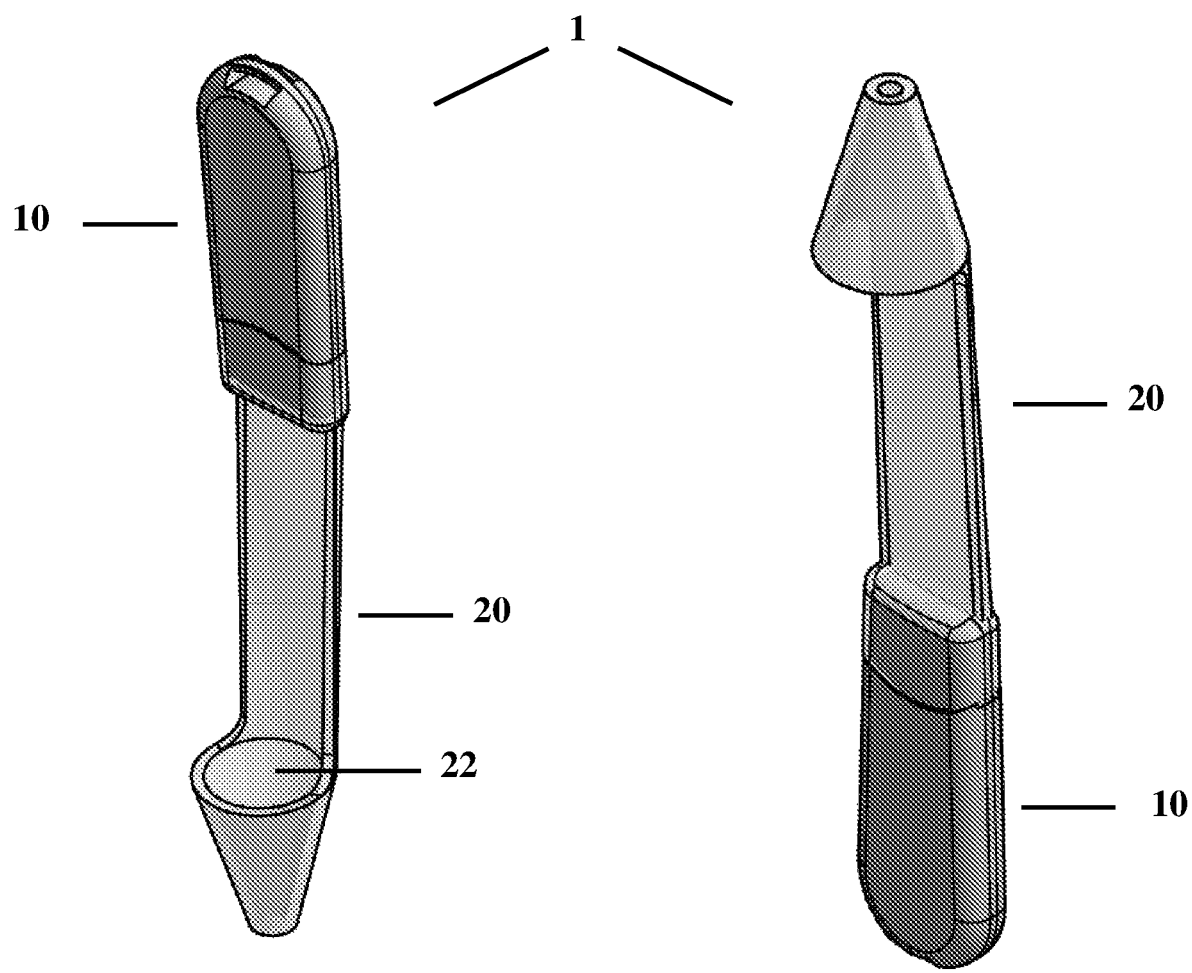
FIG. 1 shows a perspective view of a first example otoscope.
FIG. 2 shows a second perspective view of the example otoscope of FIG. 1.

Preferred features, embodiments and variations of the invention may be discerned from the following Description which provides sufficient information for those skilled in the art to perform the invention. The following Description is not to be regarded as limiting the scope of the preceding Summary of the Invention in any way.

DESCRIPTION OF EMBODIMENTS

Embodiments of the present invention will now be described with reference to FIGS. 1 to 31. In the figures, like reference numerals refer to like features.

A first exemplary otoscope 1 is illustrated in FIGS. 1-4, and features of this exemplary otoscope 1 are outlined below. The otoscope 1 includes a handle 10 and a speculum 20. The otoscope 1 is for illuminating the outer ear, especially the outer ear canal (the external acoustic meatus) and the eardrum (the tympanic membrane).

The speculum 20 extends from the handle 10 and is for directing light from the light source 12 (see FIG. 5 and as discussed below) to illuminate the outer ear. The speculum 20 includes a lens 22 for magnifying the outer ear.

Figure 5:
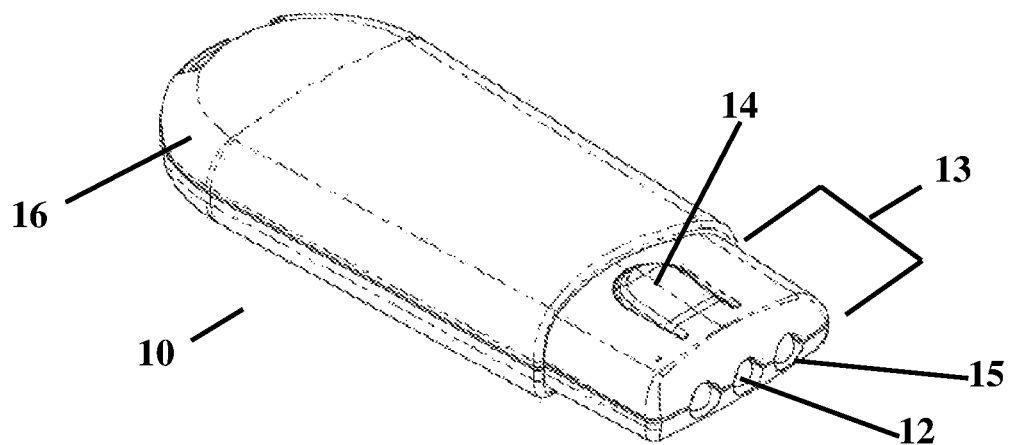
FIG. 5 shows a perspective view of the handle of the example otoscope of FIG. 1.
Figure 6:
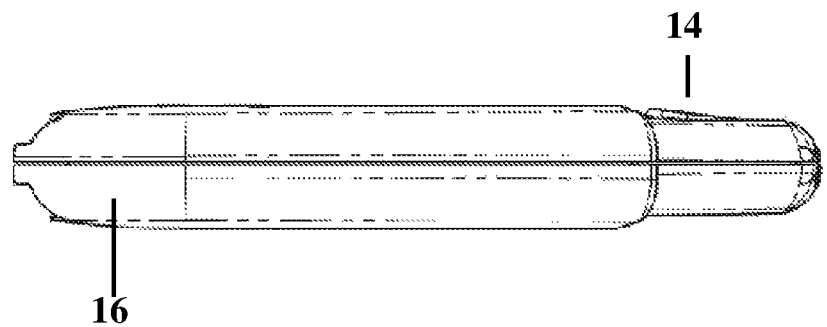
FIG. 6 shows a side view of the handle of FIG. 5.
Figure 7:
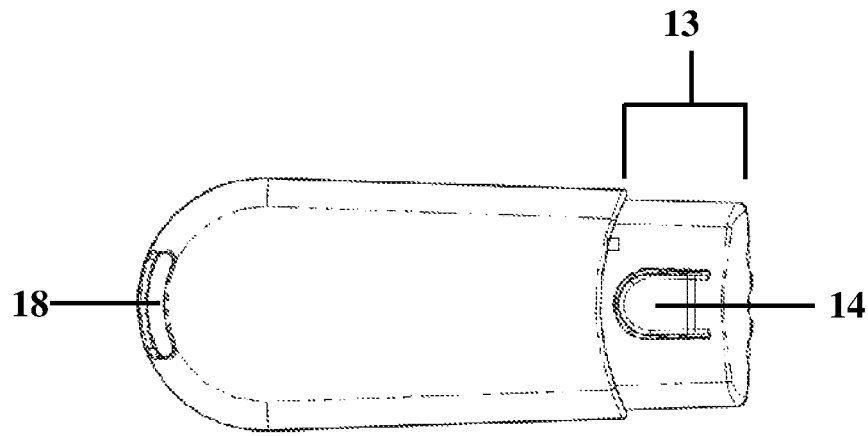
FIG. 7 shows a top view of the handle of FIG. 5.

The handle 10 of the otoscope of FIGS. 1-4 is illustrated in FIGS. 5-7. As shown in FIG. 5, the handle 10 includes three light sources 12. Light from the light source 12 passes through the speculum 20 to illuminate the outer ear.

The speculum 20 in FIGS. 1-4 is releasably engageable from the handle 10. The speculum 20 acts as an optical waveguide for light emitted from the light source 12. The speculum 20 is a solid body extending from adjacent the light source 12 to its terminal end 32. The speculum 20 of FIGS. 1-4 is adapted to emit light from the terminal end 32. The speculum 20 may be made from injection moulded plastic. The speculum 20 may be disposable.

Figures 3, 4:
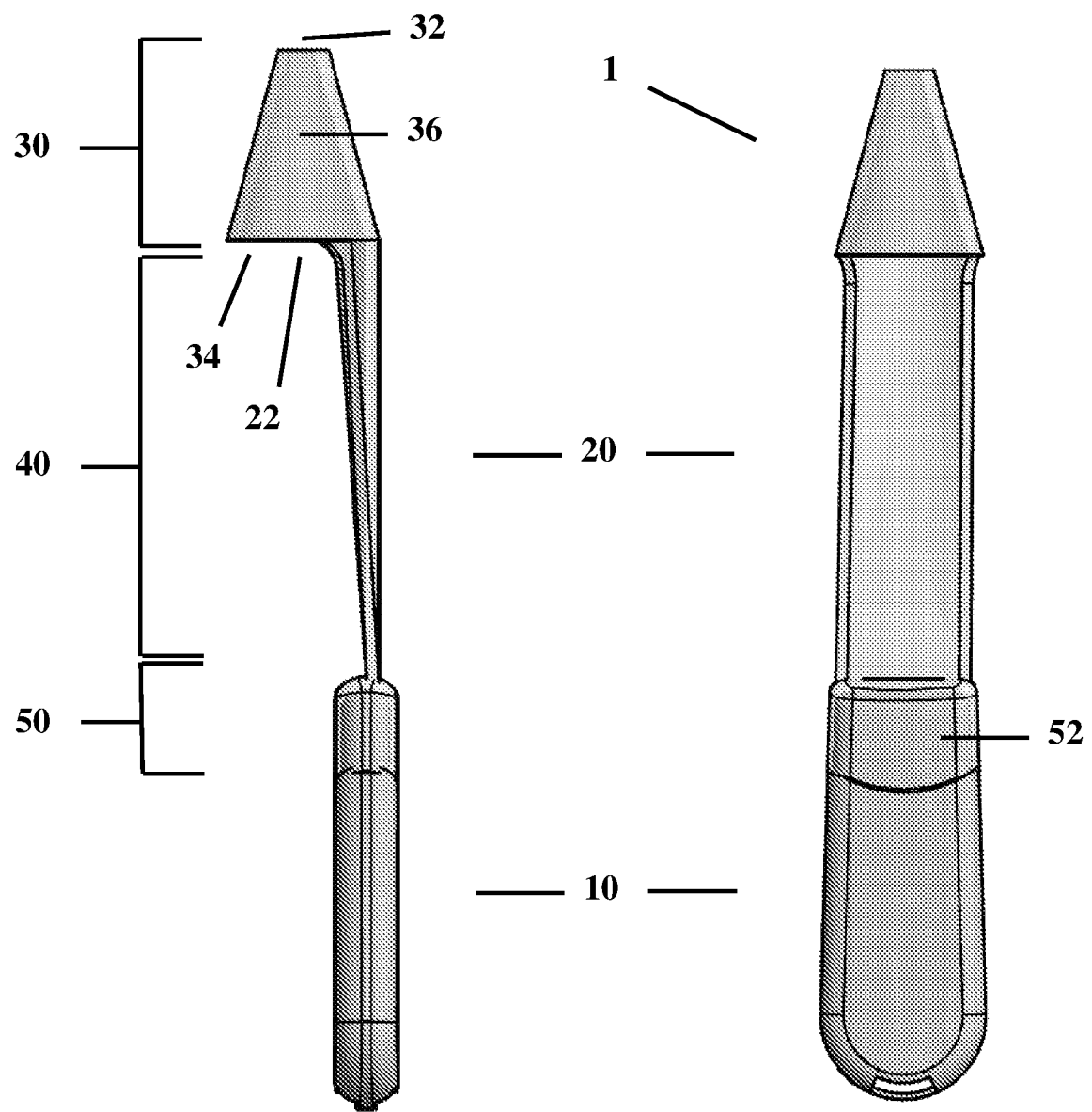
FIG. 3 shows a side plan view of the example otoscope of FIG. 1.
FIG. 4 shows a top view of the example otoscope of FIG. 1.

The speculum 20 includes a distal end portion 30 having a terminal end 32 and a non-terminal end 34 (see FIG. 3). At least a portion of the distal end portion 30 is intended to be inserted into the patient's outer ear when the otoscope 1 is used. The distal end portion includes one substantially conical side wall 36 which extends from the terminal end 32 to the non-terminal end 34. The side wall 36 defines a visualisation passageway through the distal end portion 30. The distal end portion 30 defines an aperture at the terminal end 32 and includes a lens 22 at the non-terminal end 34. The lens 22 abuts or adjoins side wall 36 and is integral with the speculum 20. The lens 22 is convex.

The speculum also includes a medial portion 40 and a proximate end portion 50 (see FIG. 3). The medial portion 40 transitions from flat to increasingly curved in a lateral direction as the medial portion 40 extends from the proximate end portion 50 to the distal end portion 30 (see FIGS. 3 and 4). The medial portion 40 in the speculum of FIGS. 1-4 is substantially flat in a longitudinal direction.

The proximate end portion 50 of the speculum is slideably engageable with the attachment-coupling portion 13 of the handle 10 (see FIGS. 5-7). The proximate end portion 50 includes a cavity 52 into which the attachment-coupling portion 13 of the handle is located. The internal walls of the cavity 52 are smooth.

The handle 10 includes a switch to connect a power supply (not shown) to the light source 12. Coupling the speculum 20 to the handle 10 actuates the switch so that light emitted from the light source 12 is transmitted by the speculum 20 to the outer ear when the handle 10 and speculum 20 are coupled together.

The attachment-coupling portion 13 includes an outer wall having a flap 14, and the flap 14 is positioned over the switch, so that depression of the flap 14 by sliding the attachment-coupling portion 13 into cavity 52 actuates the switch and activates the light source 12.

The light source 12 is located entirely within the handle 10. The light source is positioned adjacent to an opening 15 in the attachment-coupling portion 13 so that light from the light source 12 passes through the opening 15 and into the speculum 20. The handle 10 includes three light sources 12 which are positioned to extend laterally across the handle 10. The light sources 12 are especially light-emitting diodes (LEDs).

The power source in the handle 10 is in the form of a battery. The battery is especially a lithium-ion battery. The battery is connected to the light source 12 and the switch via a circuit board (not shown). The handle 10 includes a removable cover 16 for allowing the battery to be removed and replaced, as required. The removable cover 16 includes an aperture 18 providing an attachment for a keyring. The handle 10 may be made from injection moulded plastic.

The handle 10 especially does not require sterilisation and is intended for multiple uses. The speculum 20 is either sterilisable (e.g. via heat or chemical sterilisation), or is disposable. The speculum 20 and the handle 10 may be sold separately.

A second exemplary speculum 20a and otoscope 1a is illustrated in FIGS. 8-12. The handle 10 for otoscope 1a is as described above and in FIGS. 5-7. The otoscope 1a functions as described above and speculum 20a is slideably engageable with the attachment-coupling portion 13 of the handle 10.

Speculum 20a acts as an optical waveguide for light emitted from the light source 12, and is a solid body extending from adjacent the light source 12 to its terminal end 32a. Speculum 20a is made from clear injection moulded plastic and is disposable.

Speculum 20a includes a distal end portion 30a having a terminal end 32a and a non-terminal end 34a (see FIG. 11). At least a portion of the distal end portion 30a is intended to be inserted into the patient's outer ear when the otoscope 1a is used. The distal end portion 30a includes one substantially circular side wall 36a which extends from the terminal end 32a to the non-terminal end 34a. The side wall 36a defines a visualisation passageway through the distal end portion 30a. The distal end portion 30a defines an aperture at the terminal end 32a and includes a lens 22a at the non-terminal end 34a. The lens is positioned proximate to the non-terminal end 34a.

Speculum 20a also includes a medial portion 40a and a proximate end portion 50a. The medial portion 40a is substantially flat in a lateral direction, but is curved to position the longitudinal axis of the distal end portion at about 25° relative to the longitudinal axis of the handle 10.

Figure 12:
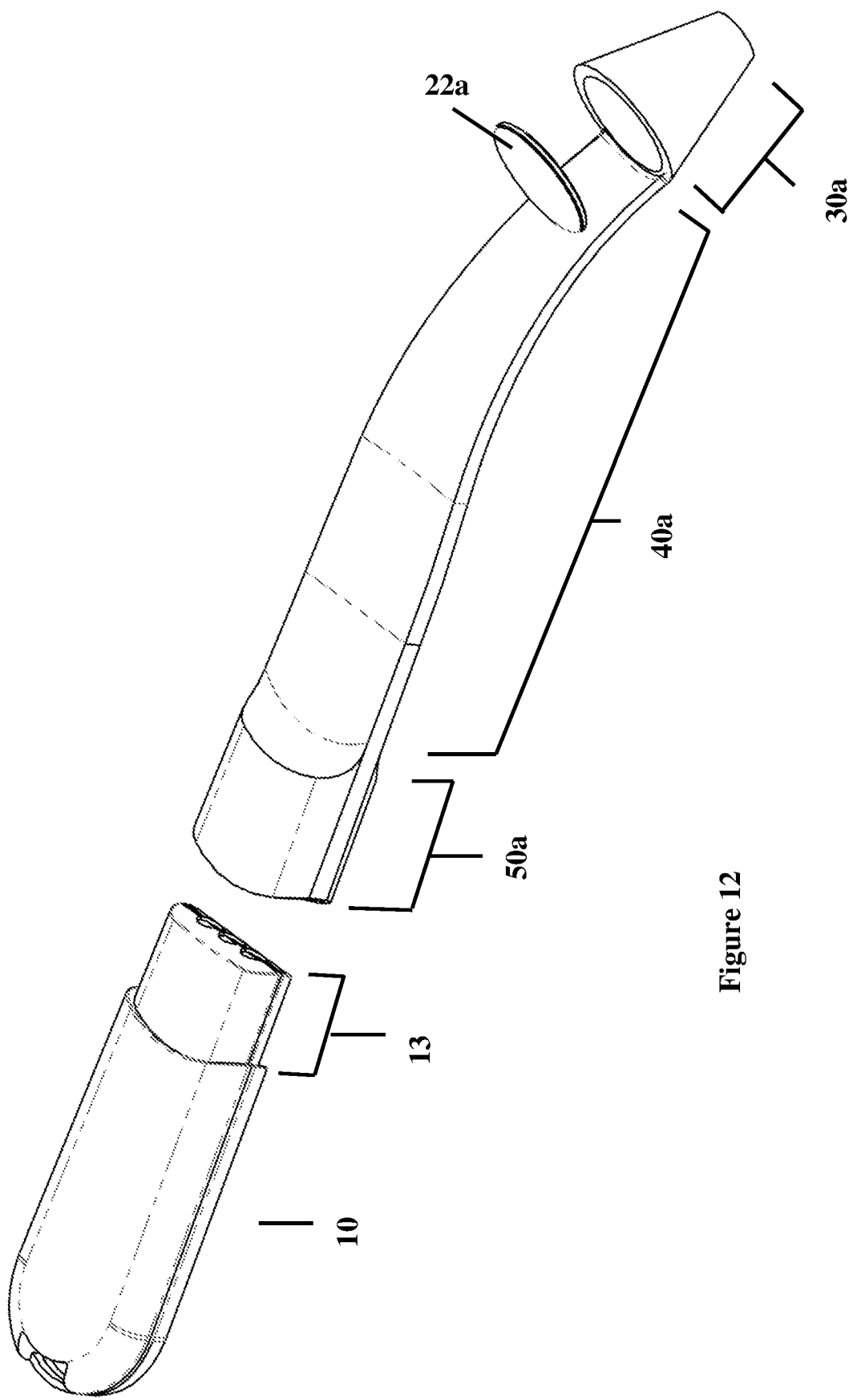
FIG. 12 shows an exploded perspective view of the otoscope of FIG. 8.

The proximate end portion 50a of the speculum is slideably engageable with the attachment-coupling portion 13 of the handle 10 (see FIGS. 11 and 12). The proximate end portion 50a includes a cavity 52a into which the attachment-coupling portion 13 of the handle is located. The internal walls of the cavity 52a are smooth.

The proximate end portion 50a includes a plurality of projections (not shown) in the form of ridges on side walls opposite to the inner side wall of the cavity 52a. These ridges are to assist a user to disengage the speculum 20a from the handle 10 by, for example, flicking the user's thumb.

A third exemplary speculum 20b and otoscope 1b is illustrated in FIGS. 13-17. The handle 10 for otoscope 1b is as described above and in FIGS. 5-7. The otoscope 1b functions as described above and speculum 20b is slideably engageable with the attachment-coupling portion 13 of the handle 10.

Speculum 20b acts as an optical waveguide for light emitted from the light source 12, and is a solid body extending from adjacent the light source 12 to its terminal end 32b. Speculum 20b is made from clear injection moulded plastic and is disposable.

Figures 13, 14, 15:
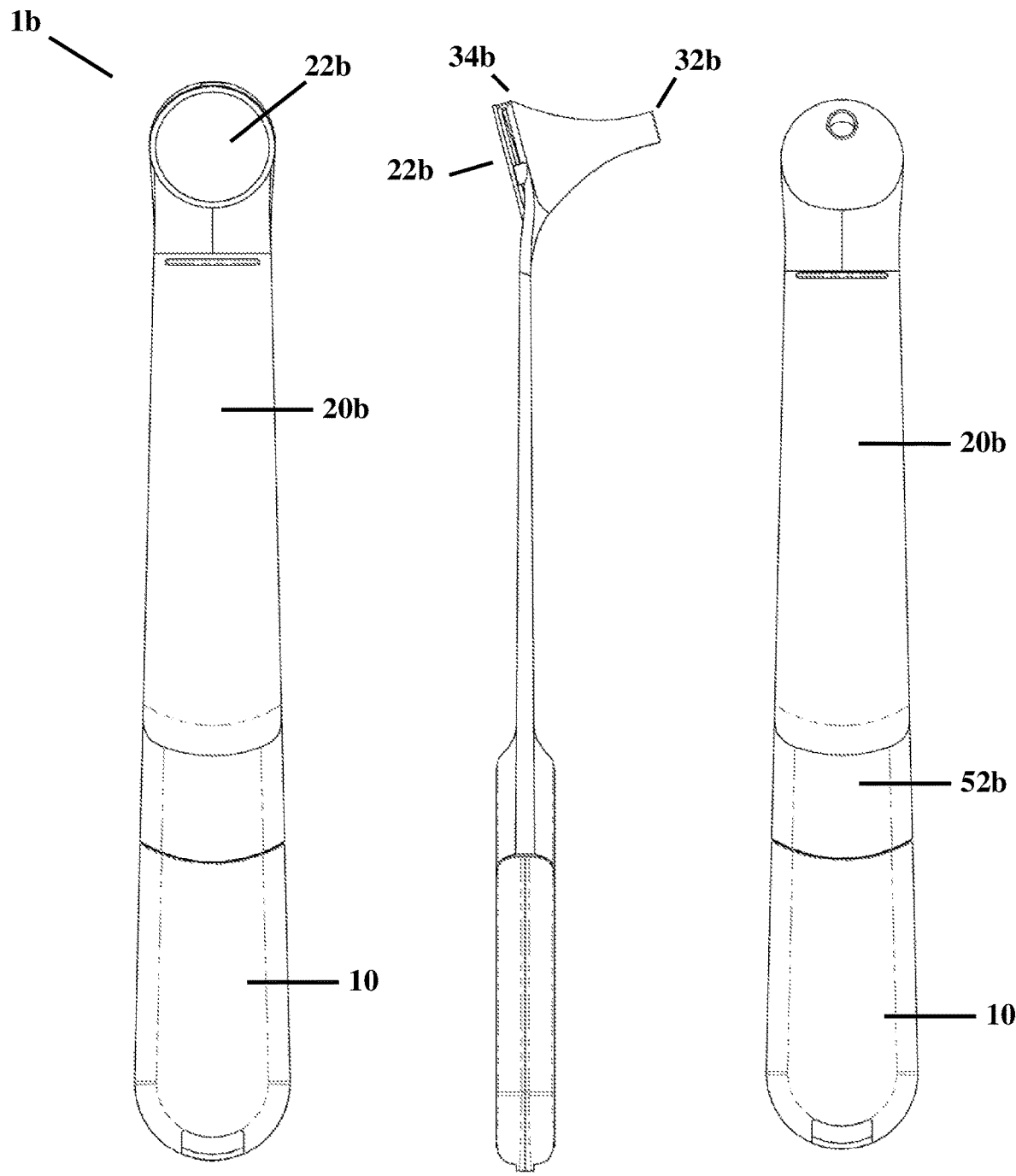
FIG. 13 shows a top view of a third example otoscope.
FIG. 14 shows a side view of the example otoscope of FIG. 13.
FIG. 15 shows a bottom view of the example otoscope of FIG. 13.

Speculum 20b includes a distal end portion 30b having a terminal end 32b and a non-terminal end 34b (see FIG. 14). At least a portion of the distal end portion 30b is intended to be inserted into the patient's outer ear when the otoscope 1b is used. The distal end portion 30b includes a side wall having a substantially conical portion 38b extending from the non-terminal end 34b, and a substantially cylindrical portion 39b extending from the terminal end 32b. The side wall 38b, 39b defines a visualisation passageway through the distal end portion 30b. The distal end portion 30b defines an aperture at the terminal end 32b and includes a lens engager 24b at the non-terminal end 34b. The lens 22b is releaseably engageable with the lens engager 24b. Once fitted, the lens 22b is positioned proximate to the non-terminal end 34b.

Speculum 20b also includes a medial portion 40b and a proximate end portion 50b. The medial portion 40b is substantially flat in a lateral and longitudinal direction. The longitudinal axis of the distal end portion 30b is at about 75° relative to the longitudinal axis of the handle 10.

The proximate end portion 50b of the speculum is slideably engageable with the attachment-coupling portion 13 of the handle 10 (see FIGS. 16-17). The proximate end portion 50b includes a cavity 52b into which the attachment-coupling portion 13 of the handle is located. The internal walls of the cavity 52b are smooth.

A fourth exemplary speculum 20c and otoscope 1c is illustrated in FIGS. 18-24. The handle 10 for otoscope 1c is as described above and in FIGS. 5-7. The otoscope 1c functions as described above and speculum 20c is slideably engageable with the attachment-coupling portion 13 of the handle 10.

Speculum 20c acts as an optical waveguide for light emitted from the light source 12, and is a solid body extending from adjacent the light source 12 to its terminal end 32c. Speculum 20c is made from clear injection moulded plastic and is disposable.

Figures 18, 19:
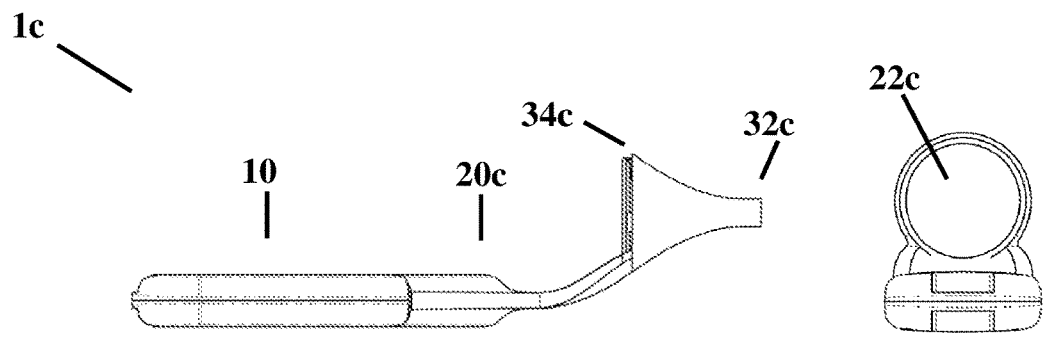
FIG. 18 shows a side view of a fourth example otoscope.
FIG. 19 shows a back view of the example otoscope of FIG. 18.
Figures 20, 21:
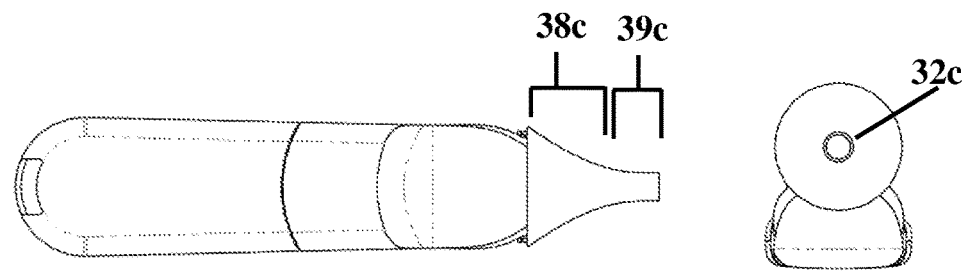
FIG. 20 shows a top view of the example otoscope of FIG. 18.
FIG. 21 shows a front view of the example otoscope of FIG. 18.
Figure 22:
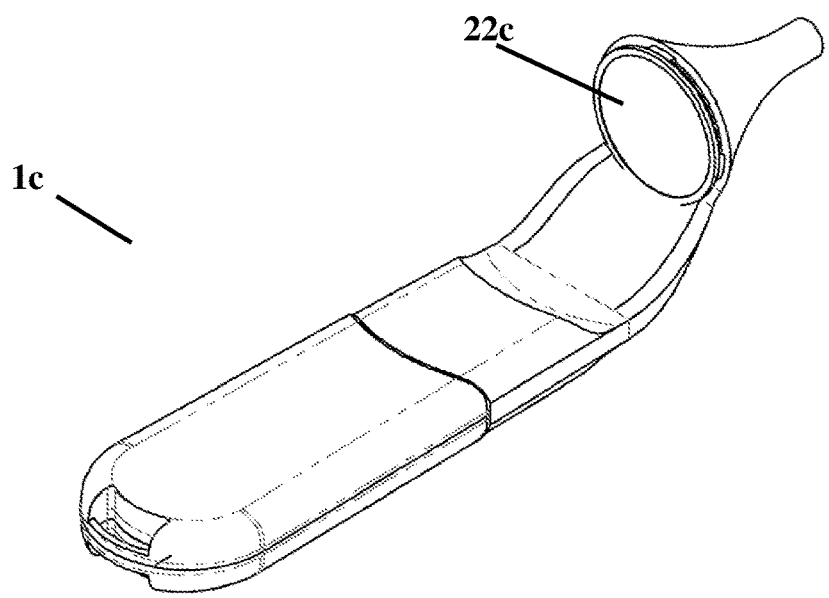
FIG. 22 shows a perspective view of the example otoscope of FIG. 18.

Speculum 20c includes a distal end portion 30c having a terminal end 32c and a non-terminal end 34c (see FIG. 18). At least a portion of the distal end portion 30c is intended to be inserted into the patient's outer ear when the otoscope 1c is used. The distal end portion 30c includes a side wall having a substantially conical portion 38c extending from the non-terminal end 34c, and a substantially cylindrical portion 39c extending from the terminal end 32c. The side wall 38c, 39c defines a visualisation passageway through the distal end portion 30c. The distal end portion 30c defines an aperture at the terminal end 32c and includes a lens engager 24c at the non-terminal end 34c. The lens 22c is releaseably engageable with the lens engager 24c. Once fitted, the lens 22c is positioned proximate to the non-terminal end 34c.

Speculum 20c also includes a medial portion 40c and a proximate end portion 50c. The medial portion 40c is curved in a lateral and a longitudinal direction. The medial portion 40c is inclined relative to the proximate end portion in a longitudinal direction. The longitudinal axis of the distal end portion 30c is substantially parallel with the longitudinal axis of the handle 10.

Figure 23:
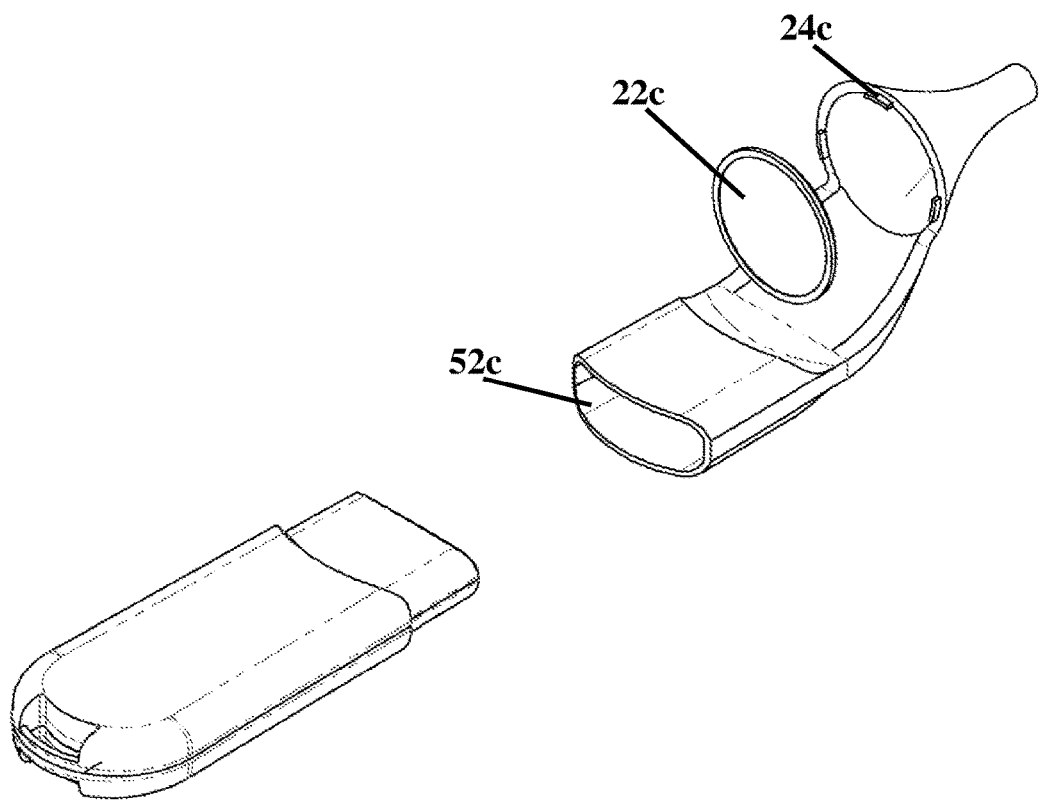
FIG. 23 shows an exploded perspective view of the example otoscope of FIG. 18.
Figure 24:
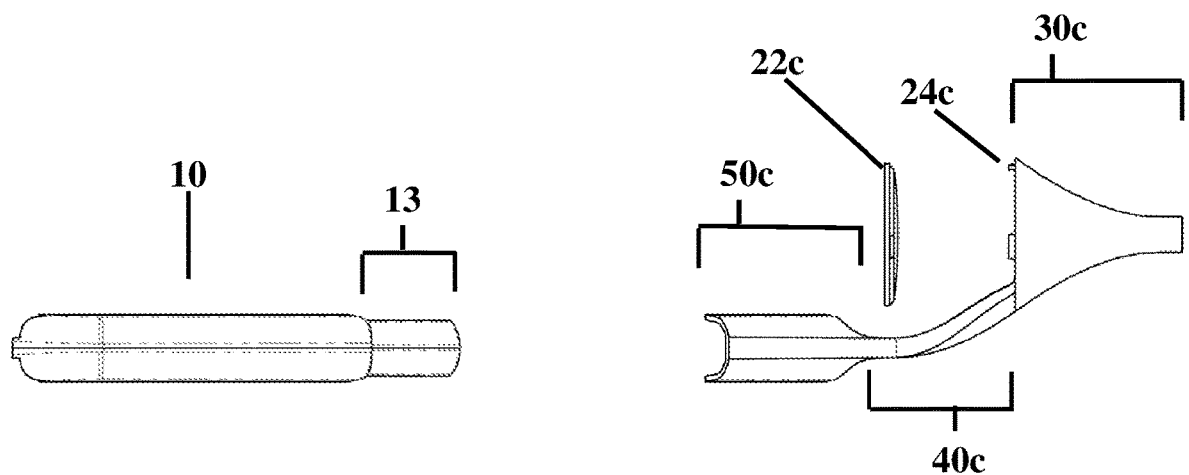
FIG. 24 shows an exploded side view of the example otoscope of FIG. 18.
Figures 25, 26:
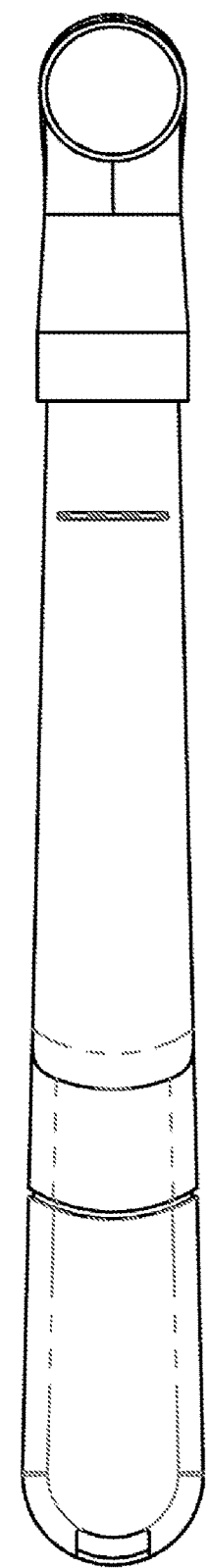
FIG. 25 shows a top view of a fifth example otoscope.
FIG. 26 shows a side view of the example otoscope of FIG. 25.

The proximate end portion 50c of the speculum is slideably engageable with the attachment-coupling portion 13 of the handle 10 (see FIGS. 23-24). The proximate end portion 50c includes a cavity 52c into which the attachment-coupling portion 13 of the handle is located. The internal walls of the cavity 52c are smooth.

To use the otoscope 1, 1a-1c the attachment-coupling portion 13 is slideably engaged into the cavity 52, 52a-52a of the speculum 20, 20a-20c. This actuates the switch and activates the light source 12, which transmits light into the speculum 20, 20a-20c. The speculum 20, 20a-20c acts as an optical waveguide to direct the light to the terminal end 32, 32a-32c of the speculum 20, 20a-20c for illuminating the patient's outer ear. At least a portion of the distal end portion 30, 30a-30c of the speculum 20, 20a-20c is then contacted with (or inserted into) the patient's outer ear, and the user views the patient's outer ear by looking through the lens 22, 22a-22c.

A fifth exemplary otoscope 1d is illustrated in FIGS. 25-31. Otoscope 1d includes a handle 10, an intermediate waveguide 120, and a speculum 20d. The handle 10 for otoscope 1d is as described above and in FIGS. 5-7. The speculum 20d is releaseably engageable with the intermediate waveguide 120, and the intermediate waveguide 120 is releaseably engageable with the handle 10.

The intermediate waveguide 120 extends from the handle 10 and is for directing light from the light source 12 (see FIG. 29) to the distal end portion of the intermediate waveguide 130.

The intermediate waveguide 120 acts as an optical waveguide for light emitted from the light source 12. The intermediate waveguide 120 is a solid body extending from adjacent the light source 12 to its distal end 132. The intermediate waveguide 120 of FIGS. 25-30 is adapted to emit light from the terminal end 132. The intermediate waveguide 120 may be made from injection moulded plastic. The intermediate waveguide 120 may be disposable or reusable.

The intermediate waveguide 120 includes a distal end portion 130 having a terminal end 132. The distal end portion 130 is substantially flat in a longitudinal and lateral direction.

Figures 27, 28:
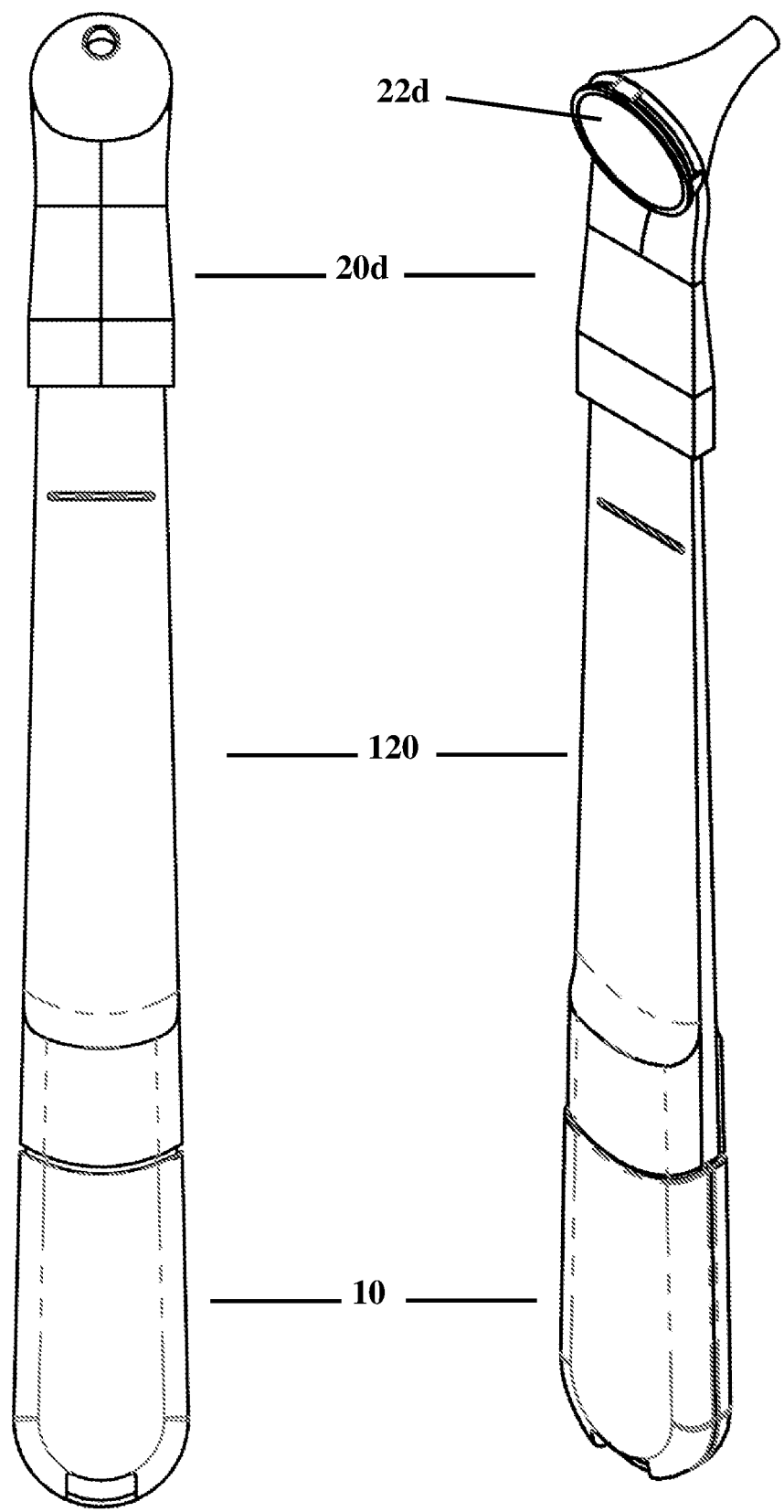
FIG. 27 shows a bottom view of the example otoscope of FIG. 25.
FIG. 28 shows a perspective view of the example otoscope of FIG. 25.
Figures 29, 30:
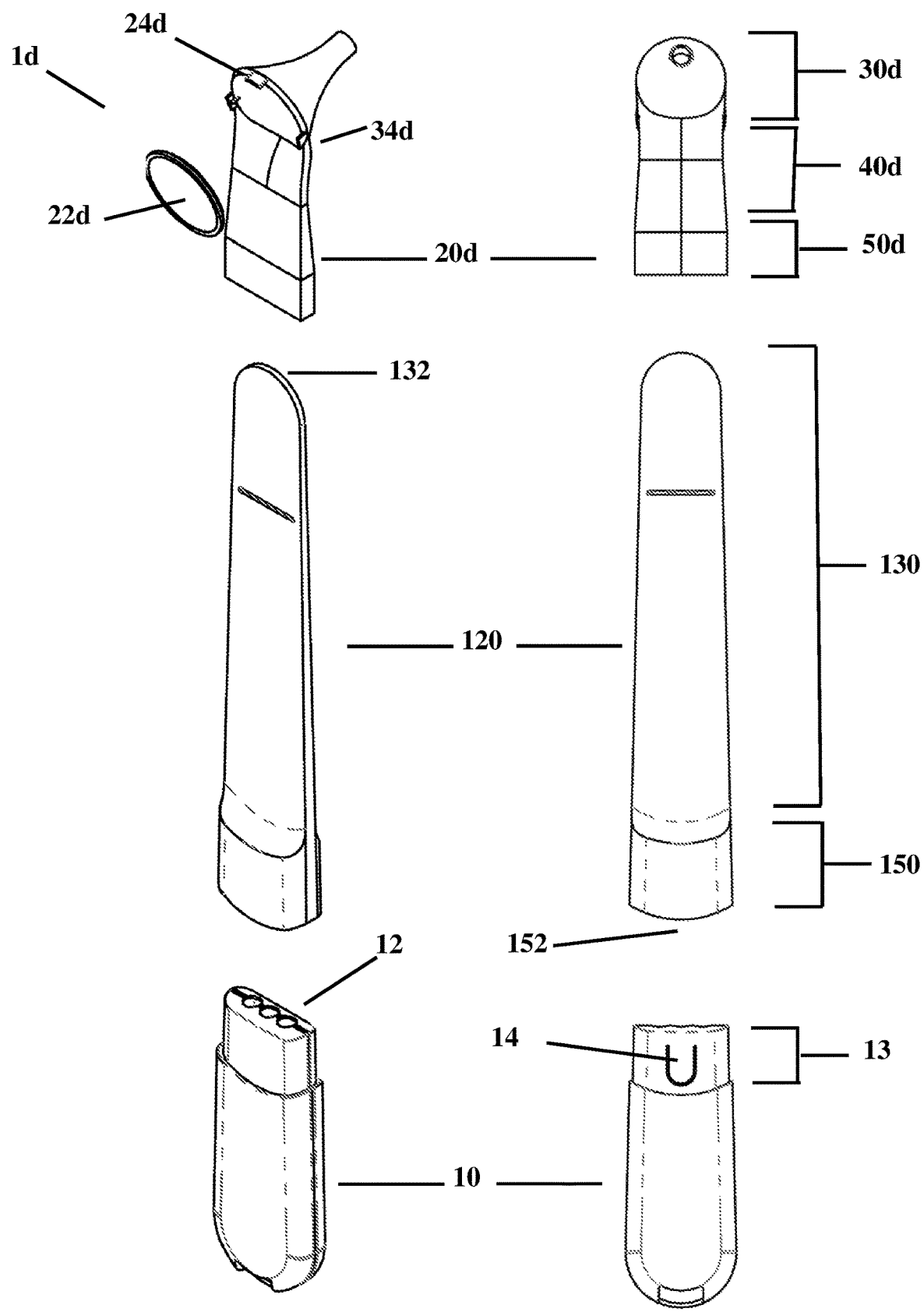
FIG. 29 shows an exploded perspective view of the example otoscope of FIG. 25.
FIG. 30 shows an exploded bottom view of the example otoscope of FIG. 25.
Figure 31:
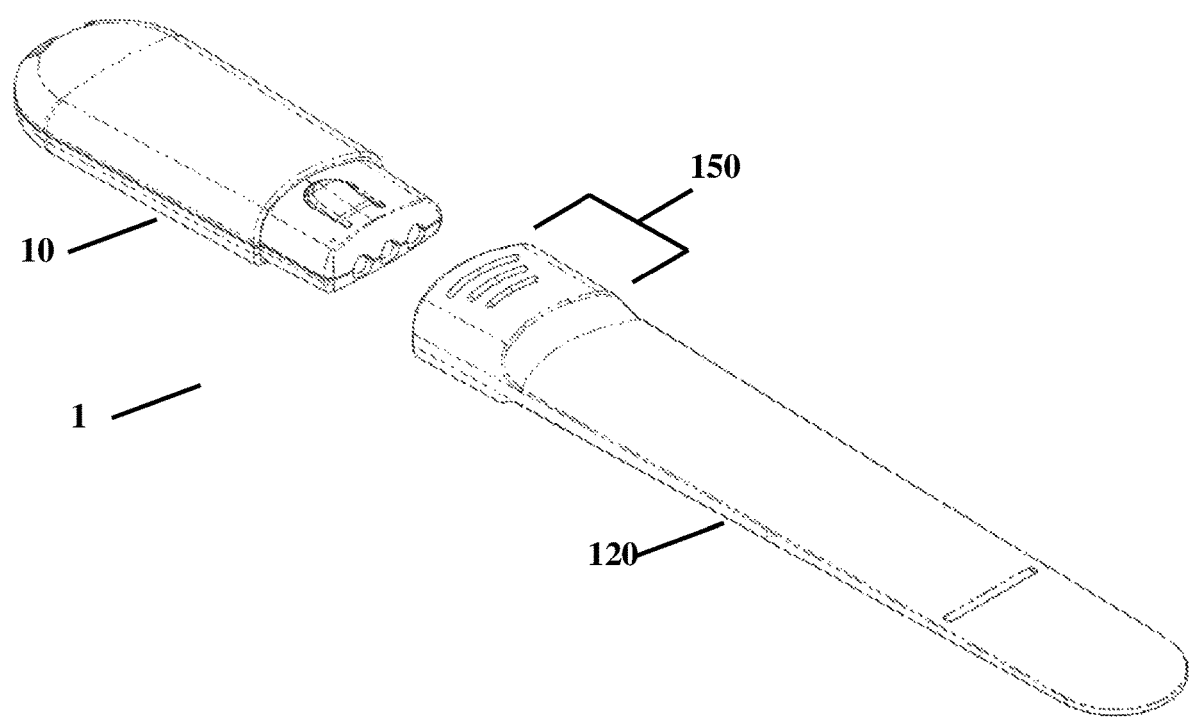
FIG. 31 shows an exploded perspective view of the handle and intermediate waveguide of the example otoscope of FIG. 25.

The intermediate waveguide 120 also includes a proximate end portion 150 (see FIGS. 27 and 30). The proximate end portion 150 of the intermediate waveguide 120 is slideably engageable with the attachment-coupling portion 13 of the handle 10 (see FIG. 30). The proximate end portion 150 includes a cavity 152 into which the attachment-coupling portion 13 of the handle is located (see FIG. 30). The internal walls of the cavity 152 are smooth.

The handle 10 includes a switch to connect a power supply (not shown) to the light source 12. Coupling the intermediate waveguide 120 to the handle 10 actuates the switch so that light emitted from the light source 12 is transmitted to the distal end portion 130 of the intermediate waveguide when the handle 10 and intermediate waveguide 120 are coupled together.

The attachment-coupling portion 13 includes an outer wall having a flap 14, and the flap 14 is positioned over the switch, so that depression of the flap 14 by sliding the attachment-coupling portion 13 into cavity 152 actuates the switch and activates the light source 12.

The speculum 20d is releaseably engageable with the distal end portion of the intermediate waveguide 130.

Speculum 20d acts as an optical waveguide for light emitted from the light source 12 and through the intermediate waveguide 120, and is a solid body extending from adjacent the distal end portion of the intermediate waveguide 130 to its terminal end 32d. Speculum 20d is made from clear injection moulded plastic and is disposable.

Speculum 20d includes a distal end portion 30d having a terminal end 32d and a non-terminal end 34d (see FIG. 30). At least a portion of the distal end portion 30d is intended to be inserted into the patient's outer ear when the otoscope 1d is used. The distal end portion 30d includes a side wall having a substantially conical portion 38d extending from the non-terminal end 34d, and a substantially cylindrical portion 39d extending from the terminal end 32d. The side wall 38d, 39d defines a visualisation passageway through the distal end portion 30d. The distal end portion 30d defines an aperture at the terminal end 32d and includes a lens engager 24d at the non-terminal end 34d. The lens 22d is releaseably engageable with the lens engager 24d. Once fitted, the lens 22d is positioned proximate to the non-terminal end 34d.

Speculum 20d also includes a medial portion 40d and a proximate end portion 50d. The medial portion 40d is substantially flat in a lateral and longitudinal direction. The longitudinal axis of the distal end portion 30d is at about 75° relative to the longitudinal axis of the handle 10 and the longitudinal axis of the proximate end portion 50d and the longitudinal axis of the medial portion 40d.

The proximate end portion 50d of the speculum is slideably engageable with the distal end portion of the intermediate waveguide 130, and especially the distal end 132 (see FIGS. 29-30). The proximate end portion 50d includes a cavity 52d into which the distal end 132 of the intermediate waveguide 130 is located. The internal walls of the cavity 52d are smooth.

To use the otoscope 1d the attachment-coupling portion 13 is slideably engaged into the cavity 152 of the intermediate waveguide 120. This actuates the switch and activates the light source 12, which transmits light into the intermediate waveguide 120. Either before or after the handle 10 and intermediate waveguide 120 are coupled together, the distal end 132 of the intermediate waveguide may be slideably engaged into the cavity 52*d* of the speculum 20*d*. The intermediate waveguide 120 and speculum 20*d* act as an optical waveguide to direct the light to the terminal end 32*d* of the speculum 20*d* for illuminating the patient's outer ear. At least a portion of the distal end portion 30*d* of the speculum 20*d* is then contacted with (or inserted into) the patient's outer ear, and the user views the patient's outer ear by looking through the lens 22*d*.

In the present specification and claims, the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims appropriately interpreted by those skilled in the art.

Advantages of the Invention

In various embodiments, the preferred embodiments of the present invention may advantageously provide one or more of the advantages listed below, when compared to typical otoscopes (especially typical pocket otoscopes):
- Improved visualisation of the patient's outer ear, especially of a greater proportion of the patient's outer ear without moving the otoscope. This may be achieved, for example, by: (i) minimisation of visual obstruction between the lens and the portion of the speculum which inserts into or contacts with a patient's outer ear; and (ii) a clear or transparent speculum.
- A lens which is positionable closer to the outer ear, which may allow use of a less powerful lens.
- Improved ease of use by actuation of the switch by simply coupling the handle and speculum together.
- Lower cost design and manufacture.

I claim:

1. An otoscope for illuminating an outer ear, the otoscope including:
   a handle including a light source; and
   a speculum including a proximate end portion releasably engageable with the handle, a distal end portion adapted to be inserted into the outer ear and a medial portion extending between the proximate end portion and the distal end portion,
   wherein the distal end portion includes a thin side wall that forms a substantially conical portion defining a passageway therethrough, the substantially conical portion extending from a non-terminal end of the distal end portion toward a terminal end thereof, and at least one of a lens for magnifying the outer ear and a lens engager for releaseably engaging the lens located proximate the non-terminal end arrangeable such that a centre axis of the lens is able to be substantially aligned with a centre axis of the substantially conical portion, and
   wherein the medial portion extends between the non-terminal end of the distal end portion and the proximate end portion and is inclined relative to the proximate end portion in a longitudinal direction, the medial portion being relatively thin in its thickness in comparison to its width,
   and
   wherein the medial portion and the thin side wall that forms the substantially conical portion of the distal end portion each include a substantially clear solid light transmissive material and are shaped such that light from the light source is guided therethrough toward the terminal end of the distal end portion thereby illuminating the outer ear.

2. The otoscope of claim 1, wherein the speculum includes the lens for magnifying the outer ear, and the lens is integral with the speculum.

3. The otoscope of claim 1, wherein the speculum includes the lens engager for releaseably engaging the lens, and the lens engager is integral with the speculum.

4. The otoscope of claim 1, wherein the outer ear includes the tympanic membrane and/or the external acoustic meatus.

5. The otoscope of claim 1, wherein the distal end portion includes a substantially cylindrical portion extending from the substantially conical portion toward the terminal end, the substantially conical portion and the substantially cylindrical portion defining the passageway through the distal end portion between the terminal and non-terminal ends.

6. The otoscope of claim 1, wherein the speculum is a solid clear body extending from the proximate end portion adjacent the light source to the terminal end of the distal end portion.

7. The otoscope of claim 1, wherein the speculum acts as an optical waveguide for light emitted from the light source.

8. The otoscope of claim 1, wherein the speculum is releasably engageable with the handle, and wherein coupling the speculum to the handle activates the light source to transmit light to the terminal end of the speculum.

9. The otoscope of claim 1, wherein the proximate end portion includes a cavity, and wherein a portion of the handle is insertable into the cavity.

10. The otoscope of claim 1, wherein the light source is located entirely within the handle.

11. A method of illuminating the outer ear of a patient, the method including the step of inserting the speculum of the otoscope of claim 1 into the outer ear of the patient.

12. The otoscope of claim 1, wherein the medial portion and distal end portion are both entirely formed of a clear light transmissive plastic.

13. The otoscope of claim 1, wherein the medial portion curves toward the distal end portion so as to curve light guided thereby toward the distal end portion.

14. The otoscope of claim 1, wherein the medial portion curves toward the distal end portion so as to direct light guided thereby toward the terminal end of the distal end portion.

15. The otoscope of claim 1, wherein the medial portion is shaped to have a transitional curvature so as to guide light to the distal end portion.

16. The otoscope of claim 1, wherein the substantially conical portion of the distal end portion includes an aperture at the non-terminal end that defines substantially the greatest cross-sectional area of the distal end portion, and wherein the at least one of the lens and the lens engager are located proximate the aperture.

17. The otoscope of claim 1, wherein the distal end portion is formed of a clear light transmissive material so as to allow viewing of the outer ear therethrough.

18. The otoscope of claim 1, wherein the relative thin medial portion is curved in a lateral direction to direct light into the thin side wall that forms the substantially conical portion.

19. The otoscope of claim 1, wherein a longitudinal axis longitudinal axis of the distal end portion is substantially parallel to a longitudinal axis of the handle, or a longitudinal axis of the proximate end portion.

20. The otoscope of claim 1, wherein a diameter of the lens is about the same as a diameter of the non-terminal end.

* * * * *